Figure 1:
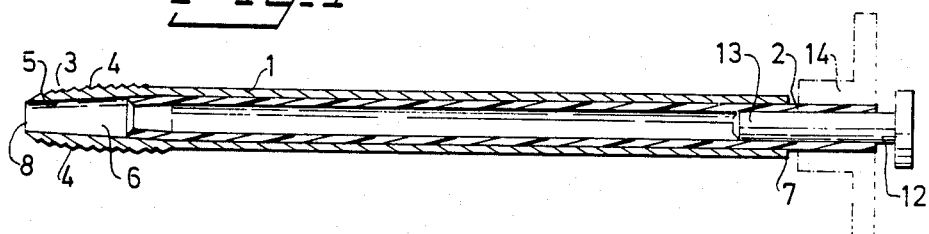

United States Patent [19]

Haglöf

[11] Patent Number: 4,733,469
[45] Date of Patent: Mar. 29, 1988

[54] EXTRACTOR FOR INCREMENT BORER

[75] Inventor: Ingvar Haglöf, LÅngsele, Sweden

[73] Assignee: Ingenjorsfirman I. Haglof AB, Solleftea, Sweden

[21] Appl. No.: 798,155

[22] Filed: Nov. 15, 1985

Related U.S. Application Data

[63] Continuation of Ser. No. 468,977, Feb. 23, 1983, abandoned.

[30] Foreign Application Priority Data

Feb. 25, 1982 [SE] Sweden .............................. 8201185

[51] Int. Cl.4 ................................................ G01N 1/04
[52] U.S. Cl. ................................... 30/130; 73/864.44; 29/278
[58] Field of Search ............. 30/130; 47/10–12, 47/50–52, 57.5; 175/20–23; 269/3–6; 73/864.41, 864.44, 864.45, 864.42, 864.51; 29/275, 278, 282

[56] References Cited

U.S. PATENT DOCUMENTS

| | | | |
|---|---|---|---|
| 715,631 | 12/1902 | Ayres | 73/864.44 |
| 1,109,446 | 9/1914 | Melberg | 73/864.44 X |
| 1,589,633 | 6/1926 | Dunton et al. | 29/275 X |
| 4,336,849 | 6/1982 | Hug | 73/864.45 X |

FOREIGN PATENT DOCUMENTS 104118  4/1964  Norway ........................... 73/864.44

Primary Examiner—Robert C. Watson
Attorney, Agent, or Firm—Nies, Webner, Kurz & Bergert

[57] ABSTRACT

An extractor for an increment borer, which consists of a tubular body having internally a cylindric portion, which at its forward end 3 transforms to a conic portion 6, and which borer on its outer surface is provided with bore threads. The extractor 2 comprises a cylindric tube, the outer diameter of which corresponds to the inner diameter of the increment borer 1, and the inner diameter of which corresponds to the smallest diameter of the increment borer 1 at the forward end 3 thereof. An indent 11, preferably a V-shaped indent, or a slit is located in the wall of the forward end 9 of the extractor 2, so that said forward end 9 is deformed plastically when this end is pressed against the said conic portion 6 of the increment borer 1.

5 Claims, 6 Drawing Figures

EXTRACTOR FOR INCREMENT BORER

This application is a continuation of application Ser. No. 468,977, filed Feb. 23, 1983, now abandoned.

This invention relates to a so-called extractor for an increment borer.

An increment borer is used for taking samples of trees. The sampling is carried out in such a manner, that an increment borer is driven in radial direction into the tree, whereafter the increment borer is screwn out. An increment borer consists of a tubular body, which is conically shaped at its forward end and provided with bore threads on its outer surface.

When the increment borer is being driven into a tree, a cylinder-shaped wood core, a so-called increment core, is pressed into the borer through an opening in the forward portion of the borer. For removing the increment core from the borer, a so-called extractor is provided, which normally consists of an axially cleft tube, which is cleft along a diameter so that a tube half is formed. This extractor is inserted into the rearward end of the increment borer between the inner wall of the increment borer and the increment core while the increment borer is in the position driven into the tree. The increment borer thereafter is turned counterclockwise, i.e. in the screwing-out direction, through about one quarter of a revolution, whereby the increment core is turned off from the forward portion of the increment borer. The extractor is provided at its forward portion with small barbs, which engage with the increment core when the extractor is being drawn out of the rearward end of the increment borer, whereby the increment core follows along resting on the semitubular portion of the extractor. The increment borer then is screwed out.

At some sampling of this type the extracted increment core is studied and thereafter thrown away or again inserted into the tree. At another type of sampling, for example at forest surveys and forest research, the increment core is to be taken along. In this case the increment core is transferred to a test tube or corresponding receptacle for further transport.

When the increment core is to be transferred to a test tube, a tube of cardboard or other transport package, the increment core, which is brittle, in extremely many cases is broken, and a new sample must be taken from the tree. As this breaking of a core occurs very usually, in many cases up to four samples must be taken before an undamaged sample lies protected in the transport package.

In many cases one does not succeed, either, in extracting an integral increment core from the increment borer.

This invention solves the aforesaid problem and offers an extractor, by which increment cores are extracted in integral state and at the same time are stored well protected.

The present invention, thus, relates to an extractor for an increment borer, which borer consists of a tubular body having internally a cylindric portion, which at its forward end transforms to a conic portion, which borer is provided on the outer surface with bore threads. The invention is characterized in that the extractor comprises a cylindric tube, the outer diameter of which corresponds to the inner diameter of the increment borer, and the inner diameter of which corresponds to the smallest diameter of the increment borer at the forward end thereof, and that an indent, i.e. a bifurcation preferably a V-shaped indent, or a slit is located in the wall of the forward end of the extractor, so that said forwaed end is plastically deformed when being pressed against said conic portion of the increment borer.

Figure 2:
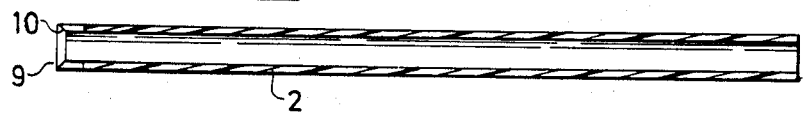
Figure 3:
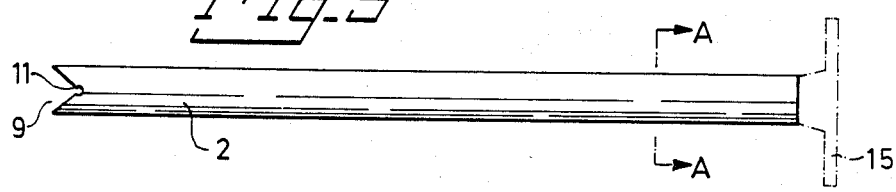
Figure 4:
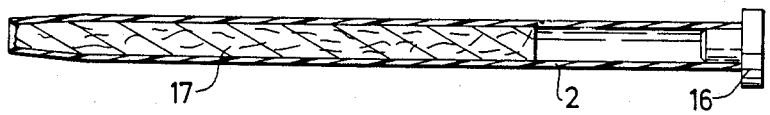
Figure 5:
Figure 6:

The invention is described in greater detail in the following, with reference to the accompanying drawing, in which FIG. 1 is an axial section of a conventional increment borer, into which an extractor according to the invention is inserted, FIG. 2 is an axial section of the extractor, FIG. 3 is a lateral view of the extractor, FIG. 4 is an axial section of an extractor according to the invention, with an increment core in the extractor, FIG. 5 is a cross-section of a conventional extractor, and FIG. 6 is a cross-section along the line A—A in FIG. 3.

A conventional extractor as described above, thus, has the cross-section shown in FIG. 5 and is manufactured of metal.

In FIG. 1 is shown, by way of an axial section, a conventional increment borer 1, into which an extractor 2 according to the invention is inserted.

The increment borer 1 is tubular and provided at its forward portion 3 with bore threads 4. The forward portion 3 has slightly conic shape on its outside 4 as well as on its inside 5. The conic portion 6 transforms to a cylindric portion, which extends to the rearward end 7 of the increment borer.

The forward opening 8 of the increment borer has a diameter which is smaller than the inner diameter of the cylindric portion. The diameter of its forward opening 8 normally is 4'2 mm while the inner diameter of the cylindric portion is 6'0 mm.

The extractor 2 according to the present invention comprises a cylindric tube, the outer diameter of which corresponds to the inner diameter of said cylindric portion, and the inner diameter of which corresponds to the diameter of the forward opening 8 of the increment borer. The length of the extractor 2 exceeds the length of the increment borer 1.

At the forward end 9 of the extractor 2, a V-shaped indent 11 is located symmetrically about a diameter of the extractor. The wall of the extractor 2 at its forward end 9, further, has a bevelled portion 10.

According to a preferred embodiment, a guide plug 12 is intended to be inserted into the rearward end of the extractor 2. Said guide plug 12 has an outer diameter corresponding to the inner diameter of the extractor 2.

For its use, the increment borer 1 is driven into a tree. When the borer has penetrated to the desired depth, the extractor 2 is inserted between the inner surface of the increment borer 1 and the outer surface of the increment core. Due to the fact, that the increment core has a diameter, which is equal or substantially equal to the inner diameter of the extractor 2, the extractor is filled by the increment core.

When the forward end 9 of the extractor 2 slides inward to the conic portion 6 of the increment borer 1, the forward end 9 of the extractor is deformed plastically to a shape corresponding to the conic portion 6. The extractor 2 is manufactured of a material capable to plastically be deformed relatively easily, preferably a plastic material.

During the insertion of the extractor 2 into the increment borer, said bevelled portion facilitates the introduction of the increment core into the extractor. During the phase when the forward portion of the extractor is deformed by the conic portion, the axial pressing force against the rearward portion of the extractor can assume substantial size. For this reason, according to a preferred embodiment, the guide plug 12 is designed to have such a length, that its forward portion 13 projects into the increment borer 1 when the forward end 9 of the extractor 2 is at the transition to the conic portion 6. The free portion of the extractor 2 hereby is stayed, so that its breaking is prevented.

After the extractor 2 has been inserted so that its forward end has been deformed, the extractor 2 is drawn out of the increment borer, after the borer had been turned back, for example, through one quarter of a revolution. In order to facilitate the drawing-out operation, the guide plug 12 can be shaped slightly conic, having its smallest diameter at its forward portion 13. Furthermore, a sleeve with a complementary shape can be provided at the rearward end of the extractor. Such a sleeve 14 is shown by dashed line in FIG. 1. The sleeve 14 is threaded onto the extractor prior to the insertion of the guide plug 12. By pulling the sleeve 14 in the direction away from the borer, the extractor is locked between the conic surfaces of the sleeve 14 and guide plug 12. As an alternative to the utilization of a sleeve 14, the extractor 2 can be formed with a collar 15 as indicated by dashed line in FIG. 3.

After the extractor has been drawn out of the increment borer, the rearward extractor end preferably is closed by means of a plastic plug 16 or the like.

The increment core 17 hereby is well protected in the extractor, which also serves as transport package.

The extractor 2 preferably is manufactured of a transparent plastic material. Experiments have proved that substantially all increment cores by working of the present invention are removed in integral state from the tree and can be transported for a long time under difficult conditions without being damaged.

As the extractor is made of a transparent material, an increment core sample can be studied in situ without having to be removed from the extractor.

The present invention, thus, solves the problems referred to above in the introductory portion. Due to the higher sampling safety, the working time is reduced substantially. Besides, no time is required for sample packaging. For this reason, the present invention is economically of importance.

The invention must not be regarded restricted to the embodiments set forth by way of example, but can be varied within the scope defined by the attached claims.

I claim:

1. An extractor for an increment borer for taking increment cores from trees, which borer consists of a tubular body, having an internal cylindrical portion which, at its forward end, transforms to a convergent conic portion, said borer being provided on its outer surface with screw threads for screwing the borer into a tree, characterized in that the extractor comprises a cylindrical tube, the outer diameter of which corresponds to the inner diameter of the cylindrical portion of the increment borer and the inner diameter of which corresponds to the smallest inner diameter of the increment borer at the forward conic end portion thereof, so that the extractor can be inserted into the borer over an increment core present in the borer, after the borer has been screwed into a tree, and that a bifurcation is located in the wall of the forward end of the extractor, so that the wall at said forward end is radially inwardly deformed plastically when said forward end is moved axially into and pressed against the said conic portion of the increment borer, and a guide plug adapted to be insertible into the rearward end of the extractor, said guide plug having a length dimension such that, when inserted in the extractor, its forward end will project into the increment borer when the forward end of the extractor is at the transition of the cylindrical portion of the increment borer to said conic portion.

2. An extractor as defined in claim 1, characterized in that it is manufactured of a transparent material.

3. An extractor for an increment borer as defined in claim 1 wherein said bifurcation at the forward end of said extractor is at least one V-shaped indent in the extractor wall.

4. An extractor for an increment borer as defined in claim 1 wherein said bifurcation at the forward end of said extractor is at least one slit in the extractor wall.

5. An extractor for an increment borer as defined in claim 1, wherein said inner diameter of the cylindrical portion of the borer and said extractor outer diameter is approximately 6.0 mm. and said extractor inner diameter and the smallest inner diameter of the increment borer at the forward conic end portion is approximately 4.2 mm.

* * * * *

UNITED STATES PATENT AND TRADEMARK OFFICE
CERTIFICATE OF CORRECTION

PATENT NO. : 4,733,469
DATED : March 29, 1988
INVENTOR(S) : INGVAR HAGLOF

It is certified that error appears in the above-identified patent and that said Letters Patent is hereby corrected as shown below:

IN THE SPECIFICATION:

Column 2, line 34, "4'2" should be --4.2--.

, line 35, "6'0" should be --6.0--.

Signed and Sealed this

Nineteenth Day of July, 1988

Attest:

DONALD J. QUIGG

Attesting Officer          Commissioner of Patents and Trademarks